(12) United States Patent
Kirsten et al.

(10) Patent No.: US 8,541,540 B2
(45) Date of Patent: Sep. 24, 2013

(54) CONTINUOUS PROCESS FOR THE EXTRACTION OF POLYAMIDE-6

(75) Inventors: Klaus Kirsten, Mainz (DE); Manfred Albrecht, Bruchkoebel (DE); Franz Samlitschka, Maintal (DE)

(73) Assignee: Lurgi Zimmer GmbH, Frankfurt am Main (DE)

( * ) Notice: Subject to any disclaimer, the term of this patent is extended or adjusted under 35 U.S.C. 154(b) by 475 days.

(21) Appl. No.: 12/542,743

(22) Filed: Aug. 18, 2009

(65) Prior Publication Data

US 2010/0048860 A1 Feb. 25, 2010

(30) Foreign Application Priority Data

Aug. 19, 2008 (DE) .......................... 10 2008 044 452

(51) Int. Cl.
*C08G 69/04* (2006.01)
(52) U.S. Cl.
USPC ........... 528/323; 528/310; 528/312; 528/480; 528/499
(58) Field of Classification Search
USPC .......................... 528/310, 312, 323, 480, 499
See application file for complete search history.

(56) References Cited

U.S. PATENT DOCUMENTS

| 4,053,457 | A | * | 10/1977 | Cordes et al. | ................. 528/323 |
| 5,674,973 | A | | 10/1997 | Pipper et al. | |
| 5,777,067 | A | | 7/1998 | Sato et al. | |
| 6,326,457 | B1 | * | 12/2001 | Erbes et al. | ................. 528/310 |
| 6,429,279 | B1 | * | 8/2002 | Hunger et al. | ................. 528/310 |
| 2003/0004305 | A1 | | 1/2003 | Haupt | |
| 2010/0237521 | A1 | | 9/2010 | Deiss | |

FOREIGN PATENT DOCUMENTS

DE 282 618 9/1990

OTHER PUBLICATIONS

Franz Fourne; Synthetic Fibers; 1999; Machines and Equipment; XP002562892; pp. 33-55 and 242-253.

* cited by examiner

*Primary Examiner* — Gregory Listvoyb
(74) *Attorney, Agent, or Firm* — Jonathan Myers; Andrew Wilford

(57) ABSTRACT

A continuous process is disclosed for the extraction of monomeric caprolactam and its oligomers as the raw polymer product obtained in the polymerization of polyamide-6 in which no fresh water, but processing water or previously used extraction water is used for the granulation.

8 Claims, 1 Drawing Sheet

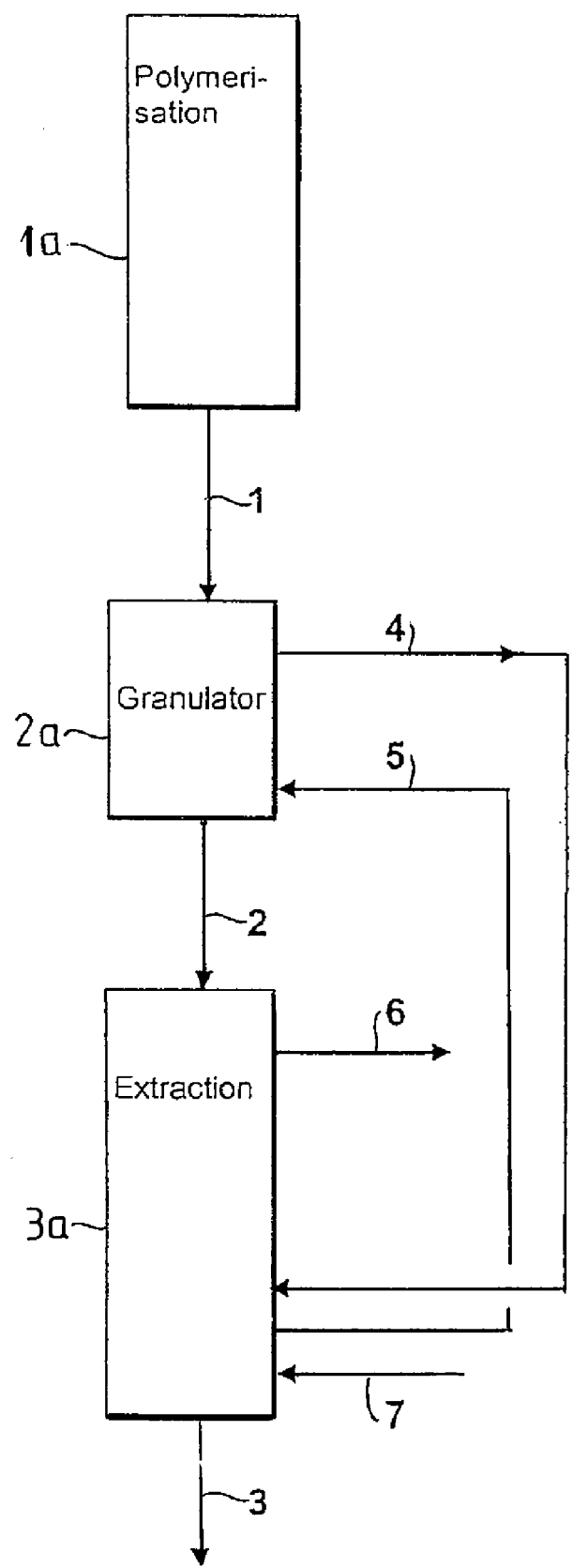

CONTINUOUS PROCESS FOR THE EXTRACTION OF POLYAMIDE-6

CROSS REFERENCE TO RELATED APPLICATIONS

This application claims the benefit of German Patent Application DE 10 2008 044452.9 filed 19 Aug. 2008, the contents of which are expressly incorporated herein by reference.

FIELD OF THE INVENTION

This invention relates to a continuous process to save energy and raw material costs in the extraction of monomeric caprolactam and its oligomers as the raw polymer product obtained in the polymerization of polyamide-6.

BACKGROUND OF THE INVENTION

The polymers created in the synthesis of polyamides by polymerizing ε-caprolactam contain low molecular components that consist of caprolactam and their oligomers. In practice, these low molecular components are removed by extraction with hot water. From these extraction waters, one can recapture the caprolactam components, clean them and perhaps introduce them again into the polymerization. It is also possible to react the oligomers obtained in the extraction waters into caprolactam by adding splitting reagents and by then isolating, washing and reusing it.

Most known procedures have the disadvantage that sometimes, the reprocessing of the extraction water must take place in several steps before the entire extraction or the extracted components, especially ε-caprolactam can be used again for polymerization. The syntheses, which suggest separation, processing and recycling of caprolactam also have the disadvantage that the oligomers contained in the extraction waters are often not reprocessed, but must be decontaminated. Moreover, in the named syntheses for reusing extraction water, the use of a processing step for hydrolytic polymerization of the extraction water concentrate or a mixture of extraction water components and caprolactam is assumed.

Depending on the temperature, the raw polymer product obtained from the polymerization of polyamide-6 contains 8-15% by weight of caprolactam in equilibrium and its oligomers. These disrupt further processing and are therefore most often removed from the polymer matrix after granulation by extraction with hot water. The water used in the process, the extraction water, is evaporated in a multi-step distillation system ("recapturing system") and the residual is put into the polymerization again as raw material.

However, in general there is a goal of keeping this amount of water as small as possible, because it requires energy to evaporate water.

In the known processes, polyamide-6 polymer is cut into cylinders or spheres in underwater granulators (UWG) or in underwater strand granulators (USG). Both types of granulators need cooling liquids in order to let the molten polymer solidify and to subsequently cool the polymer particles. This cooling liquid is normally water that is circulated in an almost closed loop.

In the course of the procedure, this water becomes enriched with caprolactam and oligomers from the polymer so that from time to time, clean water is added to the water that runs in the loop and it must be refreshed with such. Moreover, the evaporation and leakage losses must be adjusted.

Clean, most often desalinated water is added to the granulator systems. The water that is removed from the granulator system is either discarded or conveyed to the recapturing system, in order to recapture caprolactam and the oligomers. Utilization of the extraction water depends on the individual case, on the extraction content, and on the price of caprolactam and energy costs. In some cases it is more economical to discard caprolactam than to evaporate the water.

In the procedures mentioned above, technically, the continuous or also the discontinuous extraction of PA-6-chips with hot water has established itself. With this procedure, a monomer and oligomer content of <0.5% by weight are obtained in the PA-6-chip. Such low monomer and oligomer contents in polymers are required when the polyamide is to be used for spinning mill purposes.

For reasons of economy, the watery extracting solutions are processed in such a way that the valuable substances contained in them can be input as raw material into the polycaprolactam synthesis process. After simply concentrating the extraction water by evaporating the water, in addition to monomeric γ-caprolactam, the cyclical diners and additional oligomers also remain in the residual caprolactam.

In DE 2501348 B1, the concentration of the extraction water to more than 90% of the weight of the extraction amount with subsequent direct introduction into the polymerization step with and without adding fresh caprolactam is described. According to EP 0000397 B1, extraction water can also be recycled into the polymerization that was concentrated to a maximum of 60% of the extraction amount. In both cases, the extraction solutions—with or without the addition of fresh caprolactam—are adjusted in temperature prior to addition into the precondensation tube so that the cyclical diners of ε-caprolactam with high melting point remain in the solution under these conditions, so that no clogging of the pipes and the like occurs. But the splitting of the cyclical diners, which is necessary for subsequent insertion into the polymer chain can, however, not be sufficiently ensured in this way.

EP 0771834 A1 describes concentrating the extraction water with a subsequent partial ring-opening reaction of the oligomers into linear condensable compounds under reaction conditions of 230° C.-300° C. at defined pressures that are maintained up to 10 h. The thus treated extracts are subsequently polymerized together with fresh caprolactam in a reactor, whereby sometimes water concentrations of up to 10% by weight can be present. In U.S. Pat. No. 5,218,080 A, hydrolytic diner splitting of the concentrated extract is performed under pressures of 200-290° C. during a period of 2-6 h, whereby the thus obtained extract containing diners of approx. 1.3% by weight are added directly to the fresh lactam in quantities up to 10% by weight. Given the background of increasing capacity expansion of continuously operated hydrolytic caprolactam polymerization systems, the economy of these procedures and/or the amount of the residual dimer content in the extraction processed is thus in need of improvement.

Moreover, a process is known in which the extraction water after concentrating it to approx. 80% by weight, γ-caprolactam/oligomers without the addition of fresh caprolactam is polymerized in a second, separate polymerization line into PA-6 (Chemical Fibres International 47, 316 (1997)). The disadvantage of this synthesis is the high investment cost for a complete second polymerization line in which dimer reactivation takes place subject to polymerization conditions deviating from those of the fresh caprolactam polymerization process of the first line. The increased amount of water worsens the economics of this second line.

Other processes for the recovery of oligomers and cyclical diners that occur in the extraction water require separation of these components from the extraction water. U.S. Pat. No. 5,653,889 A describes a filtration technique for separating oligomers from the processing water of the PA-6 granulation. This filtration technique cannot be easily transferred to oligomer separation and processing of up to 15% by weight of watery extraction solution from the polymerization which also contains monomeric ε-caprolactam.

For the preparation of oligomers, a synthesis according to U.S. Pat. No. 4,107,160 A can be used, whereby—in addition to PA-6 solid substance waste—the oligomers are de-polymerized in the presence of a catalyst and overheated water vapor. After subsequent concentration, an approx. 50% by weight watery ε-caprolactam solution can be obtained, that is then, as per DE 4316408 A1, evaporated after a refinement step with permanganates and filtered with charcoal and evaporated; after fine distillation, the pure caprolactam that is obtained can be recycled into a PA-6 synthesis process. This costly procedure which yields a high quality of residual caprolactam, is accompanied by numerous procedural steps with correspondingly high energy consumption and materials such as permanganate and charcoal, and thus increased costs.

The alternatively possible discarding and decontamination of the oligomers that are isolated from the extraction water significantly reduces the raw material yield and thus does not represent an economical process, particularly for cases of rising system capacities.

Further, GB 1,297,263A mentions use of a catalyst for de-polymerization of the oligomers. As a possible catalyst, phosphoric acid is mentioned. What happens with the de-polymerization product is, however, not described there. Particularly, the mentioned British published patent specification does not mention a further addition of overheated water vapor into this splitting step.

In DE-A-43 21 683 and in U.S. Pat. No. 4,049,638, procedures for the synthesis of polycaprolactam are described that allow use of caprolactam with up to 15% water content in the polymerization. EP-A-0 745 631 reveals the re-use of watery extraction solutions by adding small quantities of a dicarbonic acid or polycarbonic acid, as otherwise the extract polymerizes slower than caprolactam.

As the extract also contains considerable amounts of cyclical oligomers which remain unchanged in the polymerization, several procedures for splitting these oligomers or transforming them into linear oligomers were proposed. The oligomers are usually split with phosphoric acid or by using high temperatures. Thus, U.S. Pat. No. 5,077,381 describes a procedure for splitting oligomers at temperatures of 220° to 290° C., preferably, subject to increased pressure.

Prior to returning the extraction solution into the polymerization, usually, the approximately 10% by weight extraction solution must first be processed, i.e. as a rule, it must be concentrated. Processing normally takes place by distilling the water. DE-A-25 01 348 describes the concentration process taking place in the absence of atmospheric oxygen, whereby prior to the concentrating to more than 70% of weight, fresh caprolactam is added to the extraction water, whereby the precipitation of oligomers is reduced.

In the application of the procedure for re-introducing extraction water that is mentioned above, there is, however, a severe disadvantage: The continual recirculation of the extraction water is subject to a significant increase in concentration of the oligomers and the thermodynamically stable cyclical dimers, not only in the reaction mixture, but also in the polymer, when, in the course of the continuous hydrolytic lactam polymerization, the splitting of oligomers is not successful, or the establishment of the chemical equilibrium is too slow. Moreover, the increase in oligomer concentration is particularly high when the reaction mixture—for example for the synthesis of polyamides with high molecular weight—has low water content.

OBJECTS OF THE INVENTION

It is an object of the invention to carry out the polymerization of caprolactam to form polyamide-6 using a minimum amount of energy.

It is a further object of the invention to carry out the polymerization of caprolactam to form polyamide-6 adding a minimum amount of water.

SUMMARY OF THE INVENTION

All processes known up to now have in common that large quantities of extraction water containing monomeric caprolactam and the oligomers formed by such must be introduced into a subsequent polyamide synthesis because these are raw chemical materials that are valuable. For this, the watery extraction solution must be evaporated, which is connected with high energy costs. That is why the problem is posed of finding savings in energy and raw material costs in the extraction of monomeric caprolactam and the oligomers created by such. In order to minimize the water that is to be evaporated, the circumstance is utilized that the granulation is operated with extract-containing water anyway. In accordance with the invention, no fresh water or condensate from other parts of the system is added into the cycle of the granulator system, only extract-containing water with low extract content from the extraction column.

We have discovered a continuous process for preparing polyamide-6 from caprolactam, which comprises the steps of:

(a) polymerizing caprolactam at elevated temperature to obtain a polymer melt mixture of polyamide-6, caprolactam, and oligomers of caprolactam;

(b) granulating the polymer melt mixture of polyamide-6, caprolactam, and oligomers of caprolactam to obtain chips of polyamide-6 that also contain caprolactam and oligomers of caprolactam;

(c) following step (b), extracting from the chips of polyamide-6, the caprolactam and oligomers of caprolactam, using a stream of fresh water to obtain a wet polyamide-6 product containing about 10% water by weight, a stream of extract water rich in extractable caprolactam and oligomers of caprolactam, and a first stream of recycled circulating water containing a low amount of caprolactam and caprolactam oligomers relative to the stream of extract water, and passing the first stream of recycled circulating water containing a low amount of caprolactam and caprolactam oligomers from the extraction to the granulation of step (b), whereby passing the first stream of recycled circulating water containing the low amount of caprolactam and caprolactam oligomers, as a sole source of water for the granulation, avoids any need to add fresh water to the granulation, and serves to pre-extract caprolactam and oligomers of caprolactam from the polymer melt following step (a); and (d) following the granulation of step (b) removing a second steam of recycled circulating water containing a higher amount of caprolactam and caprolactam oligomers, relative to the low amount in the first stream of recycled circulating water, and passing the second stream of recycled circulating water from the granulation to the extraction.

The steps in the process according to the invention preferably include the following:

Removal of extraction water from the lower section of the extraction column with an extract content of approximately 1 to 2%.

Use of this extraction water as processing water for the granulation until the extract content has risen to approximately 4 to 6%. Higher extract content of the granulator processing water can lead to disruptions of the granulation process.

Recirculation of the enriched processing water from the granulation into the extraction column. There, it is mixed with the processing water of the extraction column and reused up to an extract concentration of approx. 10%.

Instead of adding clean water, in accordance with the invention, "extraction water" with low extract contact, namely less than 5% by weight and at most 15% by weight of monomers or oligomers is used, preferably less than 1% by weight and at most 10% by weight of monomers or oligomers. Alternatively, processing water can also be used that accumulated in other parts of the system as condensate, for example, in the recovery or in the system component for drying granulate.

The water that has separated is then conveyed out of the granulator system into the extraction system or directly into the recovery system, where the extract that is contained in it is recovered. In this process, the water and the monomers and the oligomers are separated from each other.

The advantage of this process lies therein, that no fresh water is required for the granulator system. As a result, energy consumption is smaller and a lower consumption of raw materials occurs in the synthesis of polyamide-6, depending on whether the water from the granulator system is evaporated or discarded.

The extraction waters accumulating in the polyamide extraction have, in general, a content of organic and perhaps inorganic components of 4 to 15% by weight. In order to be able to be returned into the polymerization, these extraction waters must first be evaporated. This takes place in known manner per se in a one or a multi-step evaporation system with a short time of exposure, for example, in a Robert evaporator, fall film evaporator, thin layer evaporator or circulation evaporator. The evaporation takes place up to an extract content of at most 85% by weight, because at this concentration no precipitations of the dissolved components are observed yet. Preferably, one evaporates up to an extract content of 60 to 85% by weight, especially 70 to 85% by weight. The evaporation temperatures are thereby in general in the area of 103° C. to 115° C., preferably 107° C. to 112° C. (at normal pressure). In general, the evaporation is performed continuously.

BRIEF DESCRIPTION OF THE DRAWING

The sole FIGURE is a flow diagram showing the polymerization process to prepare polyamide-6 from caprolactam, including a polymerization stage, a granulation stage and an extraction stage as well as the recycling of process streams containing various concentrations of caprolactam and oligomers of caprolactam between the extraction stage, the granulation stage and the polymerization stage to keep energy use to a minimum.

DETAILED DESCRIPTION OF THE DRAWING

In the drawing polyamide-6 is produced as a polymer melt by polymerizing ε-caprolactam in a polymerization reactor 1a. The polyamide-6 polymer melt contains impurities including about 10% by weight unreacted ε-caprolactam and oligomers thereof. The polymer melt is then channeled through line 1 to a granulator 2a, which is preferably a strand granulator (strand pelletizer) or an underwater granulator (underwater pelletizer). In any case, the granulator includes a cooling means (not shown) to cool the molten polymer. Raw chips of polyamide-6 also containing unreacted ε-caprolactam and oligomers thereof exit the granulator through line 2, through which they are channeled to the extractor 3a. Fresh water is led into the extractor through line 7. In the extractor an extract water containing extractable amounts of caprolactam and oligomers thereof is separated from the polyamide-6 to produce an extract water rich in extractable caprolactam and oligomers thereof, which is removed from the extractor through line 6 and passed to a caprolactam recovery system (not shown), where water is evaporated from the extract water to produce a concentrated extract water containing caprolactam and oligomers of caprolactam, which may then be recycled to the polymerization reactor 1a. The polyamide-6 exits the extractor through line 3 as a moist product containing about 10% water, which may then be dried in a dryer (not shown) and then spun into fibers (not shown).

Following the extraction to remove water from the polyamide-6 chips, in which a polyamid-6 product is obtained and in which an extract water rich in caprolactam and oligomers of caprolactam is obtained, a stream of water 5 is also obtained which contains a far lower amount of caprolactam and oligomers of caprolactam than the extract water. This stream of water 5 is referred to as circulating water and is circulated from the extractor back to the granulator 2a. The stream of circulating water 5 serves as the sole source of water for the granulation, so that there is no need to introduce additional fresh water into the granulator, and thus no need to evaporate this additional water later on in the process to recover the polyamide-6 and the extractable caprolactam and oligomers of caprolactam. The stream of circulating water 5 circulated to the granulator from the extractor serves to pre-extract unreacted caprolactam and oligomers from the polyamide-6 polymer melt passing to the extractor through line 1 from the polymerization reactor.

In addition the granulator includes line 4 which directs a stream of circulating water directly to the extractor 3a. The stream of circulating water 4 contains somewhat more caprolactam and oligomers of caprolactam, than the stream of circulating water 5 from the extractor to the granulator, but nowhere near the amount of extractable caprolactam and oligomers found in the extract water which exits the extractor through line 6.

EXAMPLES

Comparative Example 1

Prior Art

Following polymerization of ε-caprolactam in a polymerization reactor, 5,500 kg of the resulting polyamide 6 are introduced per hour into a strand granulator in the form of molten polymer. There, 900 kg of fresh water is added per hour and extract-containing water for which processing is not worth it, is removed and discarded.

As a result of the circulating water, a pre-extraction of the polyamide is taking place there already, whereby the extract content or the watery caprolactam and oligomer solution that is in the cycle continually rises.

The raw granulate obtained in the strand granulator is then put into the extractor, treated with 5,500 kg of fresh water per hour and thereby, extraction water with an extract content of 10% consisting of caprolactam and oligomers is discharged. A moist polymer product is then removed from the extractor which is almost free of extract but still contains 10% water.

In all, a total quantity of 6,400 kg of fresh water or watery condensates per hour is added to the two systems, granulation and extraction.

Comparative Example 2

Prior Art

Following polymerization of ε-caprolactam in a polymerization reactor, 5,500 kg of the resulting polyamide 6 are introduced per hour in the form of molten polymer into an underwater granulator. Into the underwater granulator, 550 kg of fresh water are added per hour and a corresponding quantity of extraction water is removed.

As a result of the circulating water, a pre-extraction of the polyamide is taking place there already, whereby the extract content of the watery caprolactam and oligomer solution that is in circulation continually rises.

Out of the underwater granulator, the raw granulate is transported into the extractor and there, it is treated with 5,500 kg of fresh water per hour and a corresponding quantity of caprolactam and oligomer-containing extraction water is removed. The extraction water obtained from the underwater granulator and the extraction water obtained from the extractor are combined, washed, evaporated and the extract that is recaptured is recycled into the polymerizer. Per hour, 595 kg of extract are recaptured. A moist product is removed from the extractor which is almost extract-free, but still contains approximately 10% water.

To the two systems of granulation and extraction, a total quantity of 6,050 kg of fresh water or of watery condensates is added per hour.

Example 3

Application of the Invention by Using Strand Granulators

Following polymerization of ε-caprolactam in a polymerization reactor, 5,500 kg polyamide-6 are added per hour to a strand granulator in the form of molten polymer.

As a result of the circulating water, a pre-extraction of the polyamide is taking place there already, whereby the extract content of the watery caprolactam and the oligomer solution that is in circulation continually rises.

The raw granulate obtained in the strand granulator is then transferred to the extractor and treated with 5,500 kg of fresh water per hour or condensate from various accumulation points.

In the reverse flow to the polyamide granulate that is to be extracted, the water enriches itself with monomers and oligomers from the polyamide synthesis that detach from the polyamide granulate. At the end of the extraction process, the extraction water reaches a concentration of caprolactam and oligomers of approximately 10%.

After the water has passed through a certain stretch in the extraction pipe and has reached a concentration of approximately 0.2% of the extract, in accordance with the invention, a partial stream of 1,200 kg per hour is then removed from the extraction pipe by means of a suitable device (sieve, filter, etc.). This extract-containing water is continually added to the granulator system, where it mixes with the water that is in circulation there and lowers its extract concentration (dilutes).

The fill quantity of the granulator system is constantly controlled and the excess water that was introduced as the above mentioned partial stream, but which is not needed for balancing out insignificant evaporation and other losses, is conveyed out of the granulator cycle back into the extraction pipe.

As a result of the enrichment of extract in the granulator system and the dilution by the partial quantity that is added, the extract content of this recycled water is approximately 0.7%.

The inlet of this water into the extraction pipe is above the outlet and ideally at a level where the extract concentration of the recycled water and the water remaining in the reactor are equal.

In accordance with the invention, a total quantity of 5,500 kg of fresh water or watery condensates per hour is added into the two connected systems, granulation and extraction.

A moist polyamide-6 product is removed from the extractor that is almost free of extract and still contains approximately 10% of water.

| Example 3: Use of invention together with a strand pelletizer | | | | | | | |
|---|---|---|---|---|---|---|---|
| Stream No. | Description | PA 6 (kg/h) | Water (kg/h) | Extract (kg/h) | Sum (kg/h) | PA 6 (%) | Water (%) | Extract (%) |
| 1 | Polymer Melt | 5500 | 0 | 606 | 6106 | 90.1 | 0.0 | 9.9 |
| 2 | Raw Chips | 5500 | 5 | 600 | 6105 | 90.1 | 0.1 | 9.8 |
| 3 | Wet Product | 5500 | 600 | 11 | 6111 | 90.0 | 9.8 | 0.2 |
| 4 | Circulating Water | 0 | 1195 | 9 | 1204 | 0.0 | 99.3 | 0.7 |
| 5 | Circulating Water | 0 | 1200 | 3 | 1203 | 0.0 | 99.8 | 0.2 |
| 6 | Extract Water | 0 | 4950 | 595 | 5545 | 0.0 | 89.3 | 10.7 |
| 7 | Fresh Water | 0 | 5550 | 0 | 5550 | 0.0 | 100.0 | 0.0 |
| | | 0 | 0 | 0 | 0 | | | |
| | Consumption | 5500 kg/h Fresh Water | | | Products | 0 kg/h Waste Water | | |
| | | | | | | 5545 kg/h Extract Water to recovery/water evaporation | | |
| | | | | | | 595 kg/h Extract can be recovered | | |

Example 4

Application of the Invention by Using an Underwater Granulator

Following polymerization of ε-caprolactam in a polymerization reactor, 5,500 kg polyamide 6 are added per hour to an underwater granulator in the form of molten polymer.

In accordance with the invention, to the two connected systems of granulation and extraction a total quantity of 5,500 kg per hour of fresh water or watery condensate is added.

Per hour, 595 kg of extract are recaptured as extract water containing extractable caprolactam and oligomers of caprolactam. A moist polyamide-6 product is removed from the extractor which is almost free of extract and still contains approximately 10% water.

Example 4: use of invention together with an underwater pelletizer

| Stream No. | Description | PA 6 (kg/h) | Water (kg/h) | Extract (kg/h) | Sum (kg/h) | PA 6 (%) | Water (%) | Extract (%) |
|---|---|---|---|---|---|---|---|---|
| 1 | Polymer Melt | 5500 | 0 | 606 | 6106 | 90.1 | 0.0 | 9.9 |
| 2 | Raw Chips | 5500 | 5 | 570 | 6075 | 90.5 | 0.1 | 9.4 |
| 3 | Wet Product | 5500 | 600 | 11 | 6111 | 90.0 | 9.8 | 0.2 |
| 4 | Circulating Water | 0 | 575 | 38 | 613 | 0.0 | 93.8 | 6.2 |
| 5 | Circulating Water | 0 | 580 | 2 | 582 | 0.0 | 99.7 | 0.3 |
| 6 | Extract Water | 0 | 4950 | 595 | 5545 | 0.0 | 89.3 | 10.7 |
| 7 | Fresh Water | 0 | 5550 | 0 | 5550 | 0.0 | 100.0 | 0.0 |
| | | 0 | 0 | 0 | 0 | | | |
| | Consumption | | 5500 kg/h Fresh Water | | Products: | 0 kg/h Waste Water 5545 kg/h Extract Water to recovery/water evaporation 595 kg/h Extract can be recovered | | |

As a result of the circulating water, a pre-extraction of the polyamide takes place there already, whereby the extract content of the watery caprolactam and oligomer solution of the water that is in circulation there continually rises.

The raw granulate that is obtained in the underwater granulator is then transported to the extractor and treated with 5,500 kg of fresh water or condensate per hour from various accumulation points.

In the counter flow to the polyamide granulate that is to be extracted, the water enriches itself with monomers and oligomers of the polyamide synthesis that were detached from the polyamide granulate. At the end of the extraction process the extract water reaches a concentration of caprolactam and oligomers of approximately 10%.

After the water has passed through a certain stretch in the extraction pipe and has attained a concentration of approximately 0.3%, in accordance with the invention, a partial stream of 580 kg per hour is removed from the extraction pipe by means of a suitable device (sieve, filter, etc.). This extract-containing water is continuously conveyed to the granulator system, where it mixes with the water that is in circulation there and lowers its extract concentration (dilutes).

The fill quantity of the granulator system is constantly regulated and the excess water which was added as the partial stream mentioned above but was not needed for adjusting insignificant evaporation and other losses, is conveyed out of the granulator cycle back to the extraction pipe.

As a result of the enrichment of extract in the granulator system and the dilution by the partial quantity that was added, the extract content of this recycled water is approximately 6.2%.

The inlet of this water into the extraction pipe is above the outlet and ideally at a height where the extract concentration of the recycled and the water that remained in the reactor are equal.

Descriptions:
Extract Water Process water with a content of extractables of about 10%, sent to recovery unit/evaporation of the water
Fresh Water Demineralized water from the generation plant or from different sources within the plant (drying section . . . )
Polymer Melt Molten (liquid) PA 6, containing approximately 10% extractable components
Raw Chips Solid PA 6 chips, containing approximately 10% of extractable components
Wet Product PA 6 chips after extraction process, nearly free of extractables, but containing approximately 10% water
Circulating Water Water, containing extractables, which comes from the processes and is fed back to the process
Waste Water Process water which contains extractables in low concentrations. The recovery of the extractables is not economical and the water is sent to the waste water treatment
Extract Caprolactam and oligomers from the production of PA 6

What is claimed is:
1. A continuous process for preparing polyamide-6 from caprolactam, which comprises the steps of:
   (a) polymerizing caprolactam at elevated temperature to obtain a polymer melt mixture of polyamide-6, caprolactam, and oligomers of caprolactam;
   (b) granulating the polymer melt mixture of polyamide-6, caprolactam, and oligomers of caprolactam to obtain chips of polyamide-6 that also contain caprolactam and oligomers of caprolactam;
   (c) following step (b), extracting from the chips of polyamide-6, the extractable caprolactam and oligomers of caprolactam, using a stream of extraction water having at most 15% by weight of caprolactam monomers or oligomers to obtain a wet polyamide-6 product containing about 10% water by weight, a stream of extract water rich in extractable caprolactam and oligomers of caprolactam, and a first stream of recycled circulating water containing a low amount of caprolactam and caprolac- tam oligomers relative to the stream of extract water, and passing the first stream of recycled circulating water containing a low amount of caprolactam and caprolactam oligomers from the extraction to the granulation of step (b), whereby passing the first stream of recycled circulating water containing the low amount of caprolactam and caprolactam oligomers, as a sole source of water for the granulation, avoids any need to add fresh water to the granulation, avoids any need to evaporate said water to recover the polyamide-6, the extractable caprolactam and the oligomers of caprolactam and serves to pre-extract caprolactam and oligomers of caprolactam from the polymer melt following step (a); and (d) following the granulation of step (b) removing a second stream of recycled circulating water containing a higher amount of caprolactam and caprolactam oligomers in the range of 4 to 6%, relative to the low amount in the first stream of recycled circulating water, and passing the second stream of recycled circulating water from the granulation to the extraction.

2. The process defined in claim 1, wherein according to step (c), the first stream of recycled circulating water containing the low amount of caprolactam and caprolactam oligomers contains about 1 to 2% by weight of caprolactam and caprolactam oligomers.

3. The process defined in claim 1, wherein according to step (c), the first stream of recycled circulating water containing the low amount of caprolactam and caprolactam oligomers contains less than 1% by weight of caprolactam and caprolactam oligomers.

4. The process defined in claim 1, wherein following step (c) the wet polyamide-6 product containing about 10% water by weight is dried to produce a dry polyamide-6 and a condensate.

5. The process defined in claim 1 wherein following step (c) the stream of extract water rich in extractable caprolactam and oligomers of caprolactam has a concentration of caprolactam and oligomers of caprolactam of about 4 to 15% by weight.

6. The process defined in claim 5 wherein the stream of extract water rich in extractable caprolactam and oligomers of caprolactam has a concentration of caprolactam and oligomers of caprolactam of about 10% by weight.

7. The process defined in claim 5 wherein following step (c) the stream of extract water rich in extractable caprolactam and oligomers of caprolactam is channeled to a caprolactam recovery process for separating caprolactam from water by evaporation at 103 to 115° C., the recovered caprolactam is concentrated to a range of 60 to 85% by weight and returned to the polymerization of step (a).

8. The process defined in claim 1 wherein according to step (c) the first stream of recycled circulating water containing a low amount of caprolactam and caprolactam oligomers, relative to the stream of extract water, has an extract content of approximately 1 to 2%.

* * * * *